(12) United States Patent
Ehara et al.

(10) Patent No.: US 9,140,664 B2
(45) Date of Patent: Sep. 22, 2015

(54) LIQUID CHARACTERISTIC ANALYZING APPARATUS

(75) Inventors: Katsunobu Ehara, Kyoto (JP); Yoshihiro Tarui, Kyoto (JP)

(73) Assignee: HORIBA, LTD. (JP)

( * ) Notice: Subject to any disclaimer, the term of this patent is extended or adjusted under 35 U.S.C. 154(b) by 489 days.

(21) Appl. No.: 13/517,308

(22) PCT Filed: Dec. 15, 2010

(86) PCT No.: PCT/JP2010/072540
§ 371 (c)(1),
(2), (4) Date: Jun. 20, 2012

(87) PCT Pub. No.: WO2011/078028
PCT Pub. Date: Jun. 30, 2011

(65) Prior Publication Data
US 2012/0255347 A1    Oct. 11, 2012

(30) Foreign Application Priority Data

Dec. 25, 2009    (JP) .................................. 2009-295404

(51) Int. Cl.
*G01N 29/00*    (2006.01)
*G01N 27/416*   (2006.01)
(Continued)

(52) U.S. Cl.
CPC ........ *G01N 27/4167* (2013.01); *B01F 13/0818* (2013.01); *B01F 15/0022* (2013.01); *B01F 15/00266* (2013.01)

(58) Field of Classification Search
USPC ....................................................... 73/64.53
See application file for complete search history.

(56) References Cited

U.S. PATENT DOCUMENTS 6,057,773 A *  5/2000  Shukla et al. ................. 340/623
6,958,693 B2  10/2005  Rothgeb et al.
(Continued)

FOREIGN PATENT DOCUMENTS

CN    2219488 Y    2/1996
CN    1636230 A    7/2005
(Continued)

OTHER PUBLICATIONS

International Search Report for International Application No. PCT/JP2010/072540, mailed Mar. 29, 2011, with English translation.
(Continued)

*Primary Examiner* — Hezron E Williams
*Assistant Examiner* — Mark A Shabman
(74) *Attorney, Agent, or Firm* — Cantor Colburn LLP

(57) ABSTRACT

A liquid characteristic analyzing apparatus may include a sensor part to bring a sensor surface into contact with the liquid and outputs an electrical signal; a transmission part to convert the electrical signal to an electromagnetic wave signal or a sound wave signal and wirelessly output the electromagnetic wave signal or the sound wave signal; a containing body that exposes the sensor surface, contains the sensor part and the transmission part, and prevents the liquid from intruding into the inside, the containing body arranged in the container and immersed in the liquid; and close contact structures to bring a passing portion for the electromagnetic wave signal or the sound wave signal into substantially close contact with an inner wall of the container. The close contact structures may include a first magnetic part that is provided in the containing body and a second magnetic part that is arranged outside the container.

7 Claims, 5 Drawing Sheets

(51) Int. Cl.
*B01F 15/00* (2006.01)
*B01F 13/08* (2006.01)

(56) References Cited

U.S. PATENT DOCUMENTS

| | | |
|---|---|---|
| 2003/0045790 A1 | 3/2003 | Lewkowicz et al. |
| 2003/0227394 A1 | 12/2003 | Rothgeb et al. |
| 2004/0165474 A1* | 8/2004 | Nesbitt et al. ............ 366/142 |
| 2009/0048484 A1 | 2/2009 | Swain et al. |
| 2011/0004344 A1 | 1/2011 | Pinton et al. |

FOREIGN PATENT DOCUMENTS

| | | |
|---|---|---|
| CN | 101460605 A | 6/2009 |
| EP | 1243315 A1 | 9/2002 |
| FR | 2927266 A1 | 2/2008 |
| JP | 9-79874 A | 3/1997 |
| JP | 2002-14072 A | 1/2002 |
| JP | 2005-526332 A | 9/2005 |
| JP | 2008068229 A | 3/2008 |
| JP | 2008-206987 A | 9/2008 |
| JP | 2009-156670 A | 7/2009 |
| JP | 2009-273893 A | 11/2009 |
| JP | 2009-538433 A | 11/2009 |
| WO | 0079243 A1 | 12/2000 |
| WO | 03/021529 A2 | 3/2003 |
| WO | 2007005782 A2 | 1/2007 |
| WO | 2007134267 A2 | 11/2007 |
| WO | 2009/098146 A1 | 8/2009 |

OTHER PUBLICATIONS

Jose L. Gonzalez-Guillaumin et al., "Ingestible Capsule for Impedance and pH Monitoring in the Esophagus", IEEE Transactions on Biomedical Engineering, vol. 54, No. 12, Dec. 2007, pp. 2231-2236.
First Office Action for Chinese Patent Application No. 201080058287.3, dated Apr. 3, 2014, with English translation.
Extended European Search Report for Application No./Patent No. 10839261.4-1554/2518490, dated Oct. 30, 2013.
Japanese Office Action corresponding to Application No. 2010-549362; Date of Mailing: Sep. 9, 2014, with English translation.
Japanese Decision of Refusal corresponding to Patent Application No. 2010-549362; Date of Mailing: Jan. 6, 2015, with English translation.

* cited by examiner

LIQUID CHARACTERISTIC ANALYZING APPARATUS

CROSS REFERENCE TO RELATED APPLICATIONS

This is a U.S. national stage of application No. PCT/JP2010/072540, filed on 15 Dec. 2010. Priority under 35 U.S.C. §119(a) and 35 U.S.C. §365(b) is claimed from Japanese Application No. 2009-295404, filed 25 Dec. 2009, the disclosure of which are also incorporated herein by reference.

TECHNICAL FIELD

The present invention relates to a liquid characteristic analyzing apparatus that detects characteristics of liquid in a container and makes wireless communication of a result of the detection through an electromagnetic wave signal or the like.

BACKGROUND ART

Liquid characteristic analyzing apparatuses include various types, and one of them is a pH meter. A pH meter disclosed in, for example, Patent literature 1 is configured such that a columnar electrode attached with a sensor part is immersed in liquid to measure pH, and a pH meter main body that is connected to the electrode through a signal cable displays a result of the measurement.

In the case of using the pH meter to measure some liquid of which an amount is gradually increased by being added with another liquid, such as a buffer (buffer solution) in preparation, the electrode is adapted to gradually rise in level as a level of the liquid is raised. This is because a fore end part of the electrode is required to be immersed in the liquid in order to make the measurement, whereas a base end part of the electrode is required not to come into contact with the liquid in order to prevent the liquid from intruding.

CITATION LIST

Patent Literature

Patent literature 1: JPA 2009-156670
Patent literature 2: JPA 2002-014072

SUMMARY OF INVENTION

Technical Problem

However, it takes time and effort to adjust the level of the electrode, which becomes a factor preventing quick measurement. Specifically, when the liquid amount is small, the electrode is leaned in a container containing the liquid; when the liquid amount reaches a constant or more, the electrode is attached to an arm; and when the liquid amount is further increased, a height of the arm is adjusted or the arm is replaced to thereby adjust the level of the electrode.

On the other hand, as disclosed in Patent literature 2, a system that brings a sensor chip attached with a sensor part into contact with gas to detect a change in characteristics of the gas, and transmits a result of the detection to an external device through an electromagnetic wave signal to measure the characteristics of the gas is developed. However, in the case of attempting to use the system to measure characteristics of liquid, a transmitted electromagnetic wave signal attenuates in the liquid, which makes wireless communication impossible and consequently makes the measurement of the liquid characteristics difficult.

Therefore, the present invention is made in order to solve the above-described problems at once, and a main desired object thereof is to provide a liquid characteristic analyzing apparatus that can, without attenuation of an electromagnetic wave signal in liquid, certainly make wireless communication, and also simply and quickly measure characteristics of the liquid.

Solution to Problem

That is, a liquid characteristic analyzing apparatus according to the present invention is one that is configured to analyze characteristics of liquid in a container, and provided with: a sensor part that is configured to bring a sensor surface into contact with the liquid to detect the characteristics of the liquid, and outputs an electrical signal having a value corresponding to a detected value; a transmission part that is configured to convert the electrical signal to an electromagnetic wave signal, and wirelessly is configured to output the electromagnetic wave signal; a containing body that has a structure that exposes the sensor surface, contains the sensor part and the transmission part in an inside of the structure, and prevents the liquid from intruding into the inside, and is configured to be arranged in the container and immersed in the liquid; and close contact means is configured to bring a passing portion for the electromagnetic wave signal in the containing body into substantially close contact with an inner wall of the container. In addition, the characteristics of the liquid include, for example, chemical characteristics, physical characteristics, electrical characteristics, and optical characteristics, and more specifically, include pH, residual chlorine concentration, temperature, concentration, viscosity, flow rate, pressure, conductivity, absorbance, and the like. Further, the electromagnetic wave signal may be replaced by a sound wave signal.

If so, because the containing body has the waterproof structure, a whole of the containing body can be immersed in the liquid, and even if a level of the liquid is raised, it is not necessary to adjust a level of the containing body, so that the characteristics of the liquid can be simply and quickly analyzed. Further, the close contact means is configured to bring the passing portion for the electromagnetic wave signal in the containing body into substantially close contact with the inner wall of the container, and therefore without attenuation of the electromagnetic wave signal in the liquid, wireless communication can be certainly made.

If the close contact means is one adapted to bring the electromagnetic wave signal passing portion of the containing body into substantially close contact with a bottom surface inner wall of the container, the containing body is configured to be arranged at the bottom of the container, so that the sensor surface can be positioned as low as possible, and therefore even if an amount of the liquid is small, the analysis can be made.

In order to use a simple structure to easily bring the containing body into close contact, desirably, the close contact means is one provided with: a first magnetic part that is provided in the containing body; and a second magnetic part that is arranged outside the container, and is configured to, by magnetic force generated between the respective magnetic parts, attract and bring the electromagnetic wave signal passing portion of the containing body to and into substantially close contact with the inner wall of the container.

If the second magnetic part is provided in a mounting table for mounting the container; and the containing body in the container is configured to rotate on a basis of a change in magnetic force of the second magnetic part, the containing body can double as means adapted to stir the liquid.

In order to certainly make the wireless communication even during the rotation of the containing body, desirably, the passing portion is set on a rotational axis of the containing body.

If the liquid characteristic analyzing apparatus is further provided with a reception part that is arranged outside the container and receives the electromagnetic wave signal from the transmission part, wherein the reception part is provided in a portion that is in the mounting table and faces to the passing portion, the wireless communication can be more certainly made.

In order to facilitate downsizing, desirably, the mounting table is provided with a display part that displays an analysis result.

The electromagnetic wave signal may be an infrared signal. If so, a measurement result from the sensor part can be transmitted by means of, for example, modulation (such as frequency modulation or amplitude modulation) of the infrared signal, whereas by means of intensity attenuation of the infrared signal, temperature can be measured. If such a configuration is employed, in addition to improvement of measurement accuracy by temperature compensation, a reduction in the number of parts and downsizing of the containing body can be achieved because it is not necessary to provide the containing body with a temperature sensor.

If the liquid characteristic analyzing apparatus is one adapted such that a surface of the containing body is provided with a concave portion, and the sensor surface is exposed in the concave portion, liquid can be scooped with the concave portion or dropped into the concave portion to thereby make the analysis even if an amount of the liquid is extremely small.

If the containing body is configured to be separable into a first unit provided with the sensor part and a second unit provided with the transmission part, any one of the sensor part and the transmission part can be easily replaced as necessary, whereas a part not replaced can be continuously used, and therefore cost at the time of replacement can be reduced.

Other aspects of the present invention include a stirrer that is configured to rotate in a container to stir liquid in the container and is provided with a sensor part that is configured to bring a sensor surface into contact with the liquid to detect characteristics of the liquid.

Advantageous Effects of Invention

According to the present invention configured as described, wireless communication can be certainly made without attenuation of an electromagnetic wave signal in liquid, and also characteristics of the liquid can be simply and quickly measured.

DESCRIPTION OF EMBODIMENTS

In the following, one embodiment of the present invention is described with reference to the drawings.

First Embodiment

Figure 1:
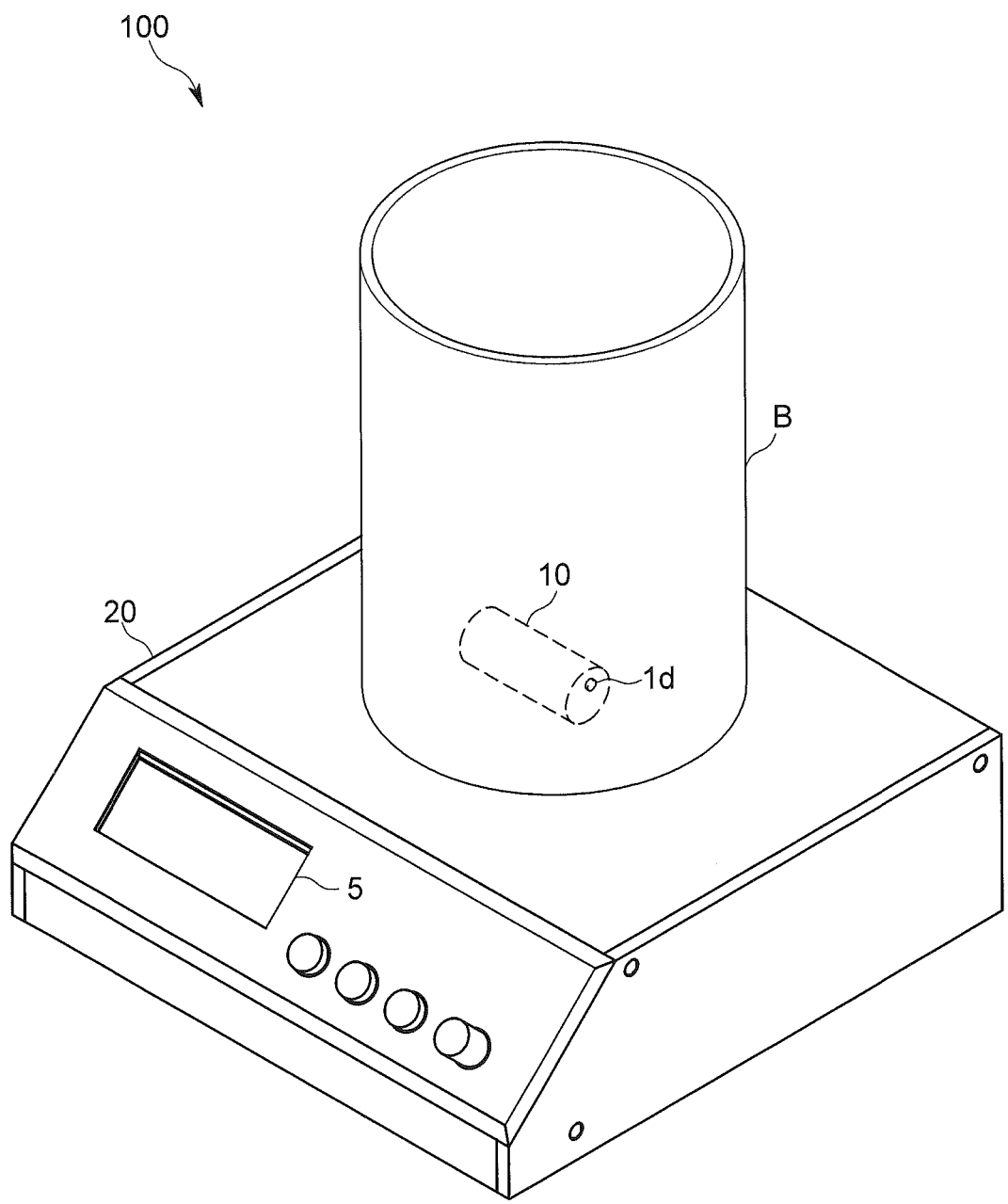
FIG. 1 is an overall perspective view illustrating a liquid characteristic analyzing apparatus in a first embodiment of the present invention.

A liquid characteristic analyzing apparatus 100 according to the present embodiment is one that measures pH of a buffer (buffer solution) in preparation, and as illustrated in FIG. 1, provided with: a containing body 10 that is arranged in a container B and immersed in liquid; and a mounting table 20 for mounting the container B. The respective parts are described in detail below.

Figure 2:
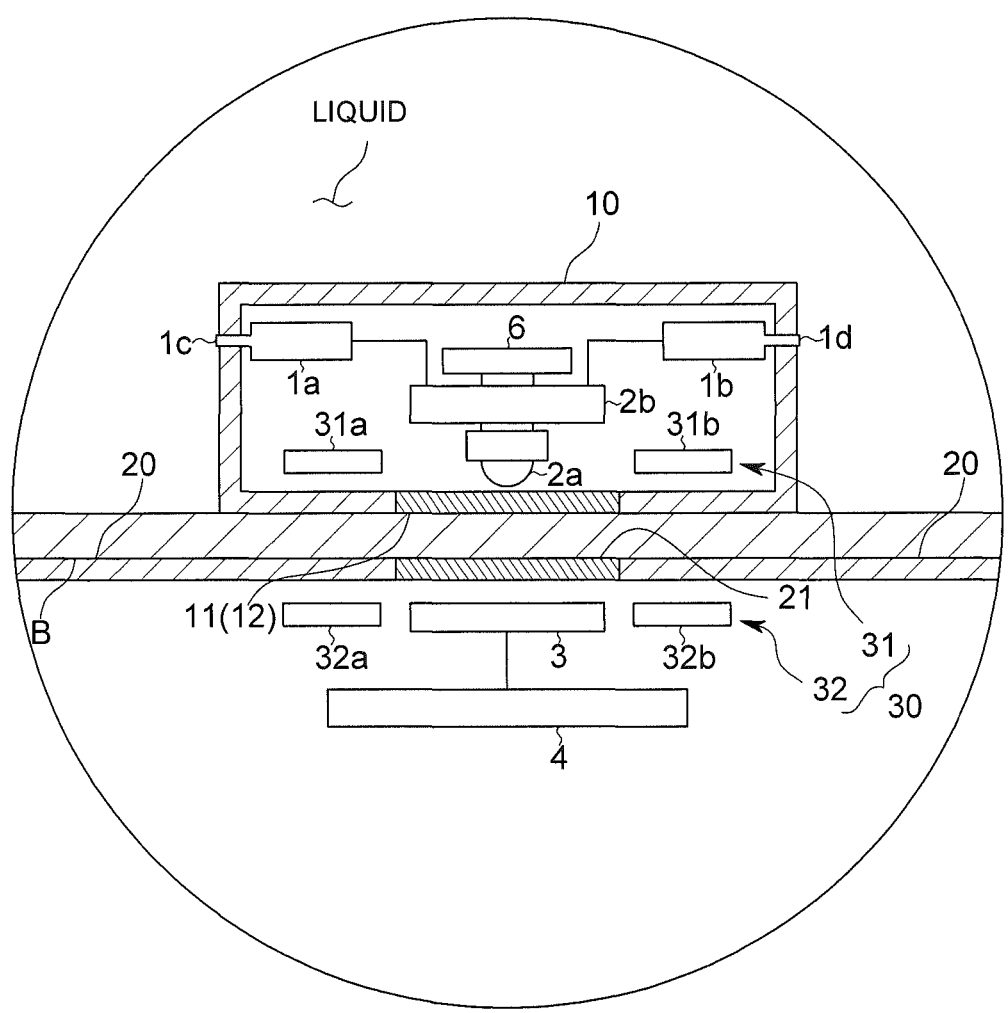
FIG. 2 is a schematic configuration diagram of the liquid characteristic analyzing apparatus in the same embodiment.

The containing body 10 is one that, as illustrated in FIG. 2 or another drawing, contains inside: a sensor part 1 that exposes only sensor surfaces 1c and 1d and is provided with electrodes 1a and 1b respectively having the sensor surfaces 1c and 1d; and a transmission part 2, and has a structure that prevents liquid from intruding inside, i.e., here, a cylindrical shape that is made of a material transmitting an infrared signal is transmitted and has both ends closed. In addition, a shape of the containing body 10 may be, besides the cylindrical shape, a capsule shape, a rectangular parallelepiped shape, or the like, and in short, the shape is only required to be a shape that can rotate in the container B to stir the liquid.

The sensor part 1 is one that, as illustrated in FIG. 2 or another drawing, brings the sensor surfaces 1c and 1d into contact with the liquid to thereby detect characteristics (here, pH) of the liquid, and outputs an electrical signal having a value corresponding to the detected value, and provided with the working electrode 1a having the sensor surface 1c and the reference electrode 1b having the sensor surface 1d. The respective electrodes 1a and 1b are configured to be separable, and when performance of each of the electrodes 1a and 1b deteriorates, or in another case, it can be replaced. From one end of the containing body 10, the sensor surface 1c of the working electrode 1a is exposed, and from the other end, the sensor surface 1d of the reference electrode 1b is exposed. In addition, as the working electrode 1a, for example, an ISFET (ion-sensitive field effect transistor), a glass electrode, or the like is cited.

The transmission part 2 is one that, as illustrated in FIG. 2 or another drawing, converts the electrical signal from the sensor part 1 to the infrared signal, and wirelessly outputs the infrared signal, and provided with a light source 2a (here, an LED) that emits the infrared signal through a transmission window 12 (here, set in the bottom surface central part of the containing body 10) that is provided in a passing portion 11 for the infrared signal in the containing body 10 and has optical transparency; and a light source control part 2b that lights the light source 2a on the basis of the electrical signal received from the sensor part 1 and is attached with a battery 6 that supplies energy for operating the respective parts of the containing body 10.

The mounting table 20 is, as illustrated in FIGS. 1 and 2, attached with a reception part 3, calculation part 4, and display part 5, and here has a substantially rectangular parallelepiped shape.

The reception part 3 is one that, as illustrated in FIG. 2 or another drawing, receives the infrared signal emitted from the transmission part 2 through a reception window 21 (here, set in the upper surface central part of the mounting table 20) that is, in the mounting table 20, provided in a portion allowing the infrared signal to pass through, and converts the infrared signal to the electrical signal to output it; provided in a portion facing to the transmission window 12; and here a photodiode. The reception window 21 is made of a material that transmits the infrared signal.

Figure 3:
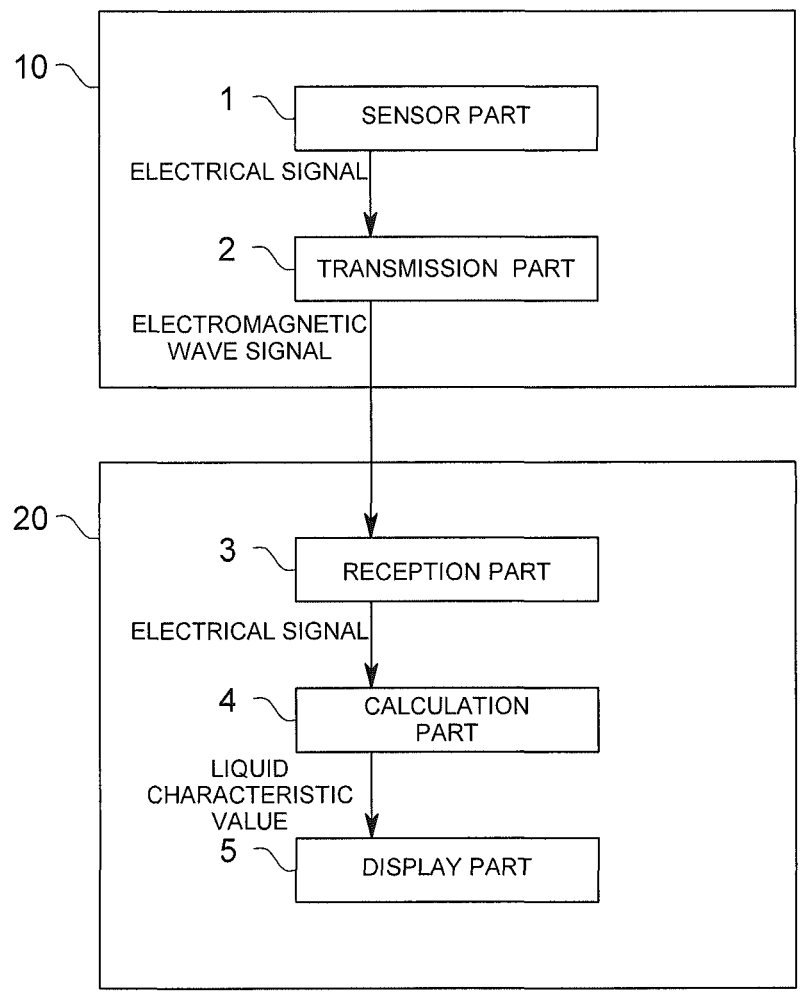
FIG. 3 is a functional configuration diagram of the liquid characteristic analyzing apparatus in the same embodiment.

The calculation part 4 is one that, as illustrated in FIG. 3 or another drawing, receives the electrical signal from the reception part 3; according to a predetermined calculation process, from the electrical signal, extracts the detected value that is a value indicating a detection result by the sensor part 1; and from the detected value, calculates a liquid characteristic value that is a value indicating the characteristics of the liquid.

The display part 5 is one that is, as illustrated in FIG. 3 or another drawing, provided on the mounting table 20 and displays an analysis result, and here displays the liquid characteristic value received from the calculation part 4.

In the present embodiment, close contact means 30 is further provided. The close contact means 30 is one that is, as illustrated in FIG. 2, provided with: a first magnetic part 31 provided in the containing body 10; and a second magnetic part 32 provided in the mounting table 20, and by magnetic force generated between the respective magnetic parts 31 and 32, the transmission window 12 provided in the infrared signal passing portion 11 of the containing body 10 is attracted to and brought into substantially close contact with an inner wall of the container B.

The first magnetic part 31 is one that, as illustrated in FIG. 2, by the magnetic force generated with the second magnetic part 32, attracts and brings the transmission window 12 for the infrared signal in the containing body 10 to and into close contact with the bottom surface inner wall of the container B, and configured with use of one or more (here, two) magnetic bodies 31a and 31b that are attached in a lower part of the containing body 10 with placing the light source 2a and a light axis of the infrared signal emitted from the light source 2a therebetween. The first magnetic part 31 is not limited to one having such an arrangement, but only required to be attached in locations close to the transmission window 12 rather than to a gravity center of the containing body 10.

The second magnetic part 32 is one that, as illustrated in FIG. 2, generates the magnetic force with the first magnetic part 31 and on the basis of a change in magnetic force of the second magnetic part 32, rotates the containing body 10 in the container B, and provided with: one or more (here, two) magnets 32a and 32b that are respectively arranged in locations that are in the mounting table 20 and face to the first magnetic part 31; and a rotor (not illustrated) attached with the magnets 32a and 32b. When the rotor is rotationally driven, the respective magnets 32a and 32b rotate to change the magnetic force applied from the second magnetic part 32 to the first magnetic part 31. On the basis of the change in magnetic force of the second magnetic part 32, the containing body 10 rotates with bringing the transmission window 12 into substantially close contact with the bottom surface inner wall of the container B, and thereby stirs the liquid in the container B. On a rotational axis of the containing body 10, the transmission window 12 and reception window 21 are arranged, and here the rotational axis of the containing body 10 and the light axis of the infrared signal emitted from the light source 2a are configured to substantially coincide with each other.

In the following, a procedure for using the liquid characteristic analyzing apparatus 100 according to the present embodiment to measure the pH of the liquid while stirring the liquid is described. When an operator presses a stirring start switch, the rotor is rotationally driven to rotate the magnets 32a and 32b of the second magnetic part 32. Then, on the basis of the change in magnetic force of the second magnetic part 32, the containing body 10 rotates to stir the liquid.

In parallel with stirring the liquid, the pH of the liquid is measured. The sensor part 1 measures the pH of the liquid, and outputs an electrical signal having a value corresponding to a measured value. The transmission part 2 converts the electrical signal to an infrared signal, and emits the infrared signal through the transmission window 12. At this time, the containing body 10 is rotating, and on the rotational axis of the rotation, the transmission window 12 of the containing body 10 and the reception window 21 of the mounting table 20 are provided. Accordingly, the emitted infrared signal reaches the reception part 3 through the reception window 21. The reception part 3 converts the infrared signal to an electrical signal; then the calculation part 4 extracts the detected value from the electrical signal to calculate the liquid characteristic value; and the display part 5 displays the liquid characteristic value.

Note that without stirring the liquid, i.e., without rotating the containing body 10, the pH of the liquid can also be measured. Also, before and after stirring the liquid, the pH of the liquid can also be measured.

According to the liquid characteristic analyzing apparatus having such a configuration, in the containing body 10, substantially, only the sensor surfaces 1c and 1d are exposed on a surface of the containing body 10 so as to come into contact with the liquid, and the other members are all contained in the containing body 10 having the water-proof structure, so that a whole of the containing body 10 can be immersed in the liquid; even if a level of the liquid is raised, it is not necessary to adjust a level of the containing body 10; and therefore the characteristics of the liquid can be simply and quickly analyzed. Further, the close contact means 30 brings the transmission window 12 provided in the passing portion 11 for the electromagnetic wave signal in the containing body 10 into substantially close contact with the inner wall of the container B, and therefore wireless communication can be certainly made without attenuation of the electromagnetic wave signal in the liquid.

Also, the first magnetic part 31 is attached in a location close to the transmission window 12 rather than to the gravity center of the containing body 10, and therefore by the magnetic force generated between the respective magnetic parts 31 and 32, the transmission window 12 of the containing body 10 and the reception part 3 can be certainly made to face to each other. Further, because the containing body 10 is cylindrically shaped, it can easily rotate and more certainly make the transmission window 12 and reception part face to each other.

Second Embodiment

Figure 4:
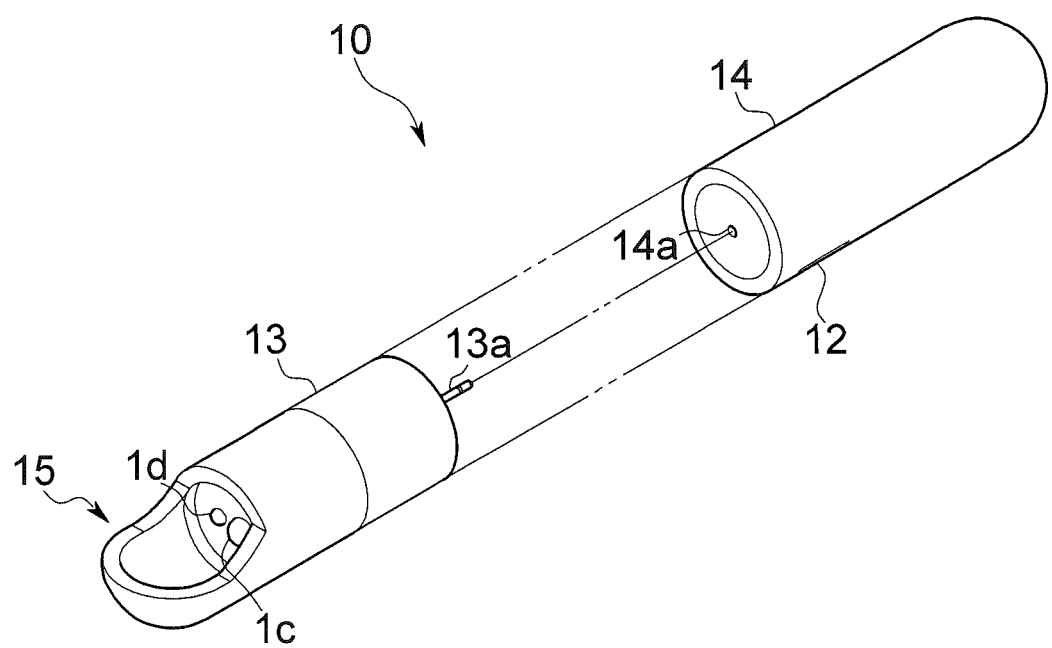
FIG. 4 is a diagram illustrating a configuration of a containing body in a second embodiment of the present invention.

A liquid characteristic analyzing apparatus 100 according to the present embodiment is provided with a containing body 10 that is, as illustrated in FIG. 4, configured to be separable into a first unit 13 provided with a sensor part 1 and a second unit 14 provided with a transmission part 2 and a first magnetic part 31, and when the respective units 13 and 14 are connected to each other, formed into a substantially capsule shape. On a surface of the first unit 13, a concave portion 15 is provided, and in the concave portion 15, sensor surfaces 1c and 1d of the sensor part 1 are exposed.

The first unit 13 has a cylindrical shape of which one end surface is a flat surface and the other end surface is a hemispherical surface, both of which are respectively closed. In the center of the one end surface, a connector 13a is provided, and on the other end surface, the concave portion 15 is provided. In the concave portion 15, the sensor surfaces 1c and 1d of the sensor part 1 are adjacently exposed.

The second unit 14 has a cylindrical shape of which one end surface is a flat surface and the other end surface is a hemispherical surface, both of which are respectively closed. In the center of the one end surface, a hole 14a to be connected with the connector 13a is provided. Note that, in the present embodiment, the first magnetic part 31 is adapted to be provided in the second unit 14; however, it may be adapted to be provided in the first unit 13 or in the respective units 13 and 14. Also, the containing body 10 is adapted to include the two units 13 and 14; however, it may be adapted to include a plurality of units.

According to the liquid characteristic analyzing apparatus 100 having such a configuration, the containing body 10 is configured to be separable as the plurality of units 13 and 14, so that, as necessary, any one of the sensor part 1 and the transmission part 2 can be easily replaced, whereas a part not replaced can be continuously used, and therefore cost at the time of replacement can be reduced.

Also, on the surface of the containing body 10, the concave portion 15 is provided, so that liquid can be scooped with the concave portion 15 or dropped into the concave portion 15, and therefore even if an amount of the liquid is extremely small, an analysis can be made.

Further, the respective sensor surfaces 1c and 1d are adjacently exposed in one and the same concave portion 15, so that it is not necessary to bring the liquid into contact with them separately, and even in the case of an extremely small amount of liquid, the analysis can be simply and quickly made.

Note that the present invention is not limited to any of the above-described embodiments. For example, at least one of the first and second magnetic parts is only required to have the magnets, whereas the other one is only required to have any of the magnets or magnetic bodies. Also, the first magnetic part may have any of the set of magnets and the set of magnetic bodies and the second magnetic part may have electromagnets, or vice versa.

In addition, the containing body is adapted to be made of the material that transmits the electromagnetic wave signal; however, it is only necessary for at least the passing portion to be one that transmits the electromagnetic wave signal, and the containing body may be made of a plurality of materials. Also, the containing body may be one that is provided with a main body of the containing body and an openable/closable open/close lid. If so, the battery that supplies the energy for operating the containing body, sensor part, or the like can be easily replaced.

In any of the above-described embodiments, as the electromagnetic wave signal, the infrared signal is used; however, without limitation to this, a radio wave, visible ray, ultraviolet ray, X-ray, gamma ray, or the like may be used. Also, not only the electromagnetic wave signal, but also a sound wave can be used.

In addition, the sensor part may be one that measure the pH of the liquid, and the electromagnetic wave signal may be the infrared signal. If so, a measurement result from the sensor part can be transmitted by means of modulation (such as frequency modulation or amplitude modulation) of the infrared signal, whereas by means of intensity attenuation of the infrared signal, temperature can also be measured. Further, it is not necessary to provide the containing body with a temperature sensor, which prevents the containing body from being increased in size, and also by correcting a pH measurement result with temperature, the pH can be highly accurately measured.

The reception part may be a fore end part of light transmitting means that is connected to a receiver.

Further, a control signal transmission part that is provided outside the container and transmits control signals (for example, an analysis start signal and an analysis end signal), and a control signal reception part that is provided inside the containing body and receives the respective signals may be provided. The control signals include the energy for operating the containing body.

Figure 5:
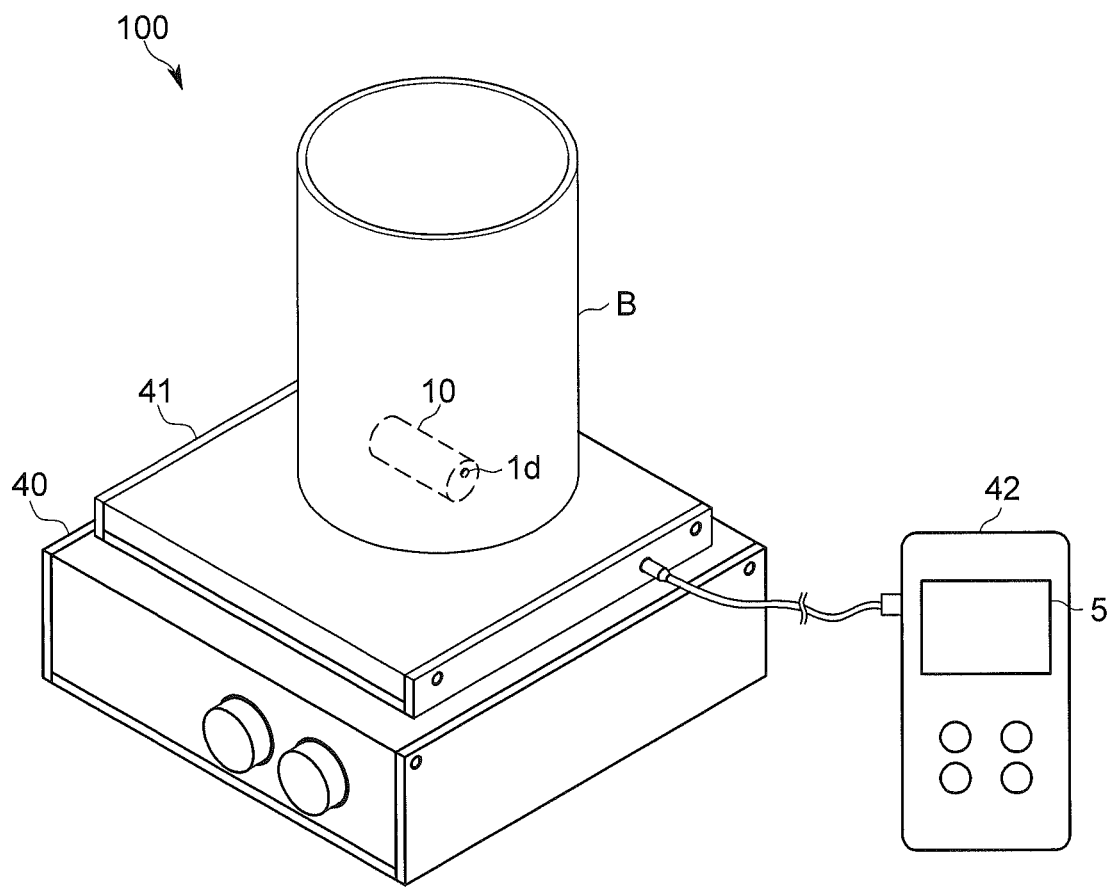
FIG. 5 is an overall perspective view illustrating a liquid characteristic analyzing apparatus in another embodiment of the present invention.

Of an existing liquid stirring device provided with: a stirrer (not illustrated) that is arranged in the container B and immersed in the liquid; and a mounting table 40 that is mounted with the container B and rotationally drives the stirrer, the mounting table 40 can also be used. In this case, the mounting table 40 is not provided with the reception part 3 and the like, and therefore it is only necessary to have a configuration, for example, as illustrated in FIG. 5. In FIG. 5, an intermediate body 41 that is arranged between the mounting table 40 and the container B, and a display 42 that is electrically connected to the intermediate body 41 are provided.

The intermediate body 41 is provided with the reception part 3 and a first calculation part (not illustrated), and configured not to block magnetic force. However, the intermediate body 41 is not limited to this, but in short, only required to be one that does not prevent the close contact or rotation of the containing body 10 by the magnetic force generated between the respective magnetic parts 31 and 32. The first calculation part is one that, according to a predetermined calculation process, from an electrical signal received from the reception part 3, extracts a detected value that is a value indicating a detection result by the sensor part 1.

The display 42 is one that is provided with a second calculation part (not illustrated) and the display part 5. The second calculation part is one that, from the detected value, calculates the liquid characteristic value that is the value indicating the characteristics of the liquid. The second calculation part and display part 5 are here assumed to be provided for the display 42; however, they may be provided for the intermediate body 41. In this case, the display 42 may not be provided.

Also, the present invention may be adapted such that the stirrer that rotates in the container to stir the liquid in the container is provided with the sensor part that brings the sensor surfaces into contact with the liquid to detect the characteristics of the liquid.

Further, the present invention may be adapted to provide the stirrer or containing body with the display part that displays a detection result, or provide a storage part (e.g., a memory) that stores a detection result, and electrically connect the storage part to a general-purpose or dedicated computer to extract the detection result.

Besides, the present invention may combine the respective configurations, and without departing from the scope thereof, can be variously modified.

INDUSTRIAL APPLICABILITY

100: Liquid Characteristic Analyzing Apparatus
1: Sensor Part
1c, 1d: Sensor Surface
2: Transmission Part
3: Reception Part
5: Display Part
10: Containing Body 11: Passing Portion
12: Transmission Window
13: First Unit
14: Second Unit
15: Concave Portion
20: Mounting Table
30: Close Contact Means
31: First Magnetic Part
32: Second Magnetic Part
B: Container

The invention claimed is:

1. A liquid characteristic analyzing apparatus that is configured to analyze a characteristic of liquid in a container, the apparatus comprising:
   a sensor part structured to bring a sensor surface into contact with the liquid to thereby detect the characteristic of the liquid, and outputs an electrical signal having a value corresponding to a detected value;
   a transmission part structured to convert the electrical signal to an electromagnetic wave signal or a sound wave signal, and structured to wirelessly output the electromagnetic wave signal or the sound wave signal;
   a containing body that has a structure that exposes the sensor surface, contains the sensor part and the transmission part in an inside of the structure, and prevents the liquid from intruding into the inside, the containing body structured to be arranged in the container and immersed in the liquid;
   close contact means structured to bring a passing portion for the electromagnetic wave signal or the sound wave signal in the containing body into substantially close contact with an inner wall of the container;
   wherein the close contact means comprises a first magnetic part that is provided in the containing body and a second magnetic part that is arranged outside the container; and
   a surface of the containing body is provided with a concave portion, and the sensor surface is exposed in the concave portion.

2. The liquid characteristic analyzing apparatus according to claim 1, wherein:
   the close contact means is structured to, by magnetic force generated between the respective magnetic parts, bring the passing portion for the electromagnetic wave signal or the sound wave signal in the containing body into substantially close contact with the inner wall of the container.

3. The liquid characteristic analyzing apparatus according to claim 2, wherein:
   the second magnetic part is provided in a mounting table for mounting the container; and
   the containing body in the container is structured to rotate on a basis of a change in magnetic force of the second magnetic part.

4. The liquid characteristic analyzing apparatus according to claim 3, wherein:
   the passing portion is set on a rotational axis of the containing body.

5. The liquid characteristic analyzing apparatus according to claim 3, the apparatus further comprising:
   a reception part that is arranged outside the container and receives the electromagnetic wave signal or the sound wave signal from the transmission part, wherein
   the reception part is provided in a portion that is in the mounting table and faces to the passing portion.

6. The liquid characteristic analyzing apparatus according to claim 1, wherein:
   the electromagnetic wave signal is an infrared signal.

7. A stirrer that is configured to rotate in a container to stir liquid in the container, the stirrer comprising:
   a sensor part structured to bring a sensor surface into contact with the liquid to thereby detect a characteristic of the liquid to thereby detect the characteristic of the liquid, and output an electrical signal having a value corresponding to a detected value;
   a transmission part structured to convert the electrical signal to an electromagnetic wave signal or a sound wave signal, and structured to wirelessly output the electromagnetic wave signal or the sound wave signal;
   a containing body that has a structure that exposes the sensor surface, contains the sensor part and the transmission part in an inside of the structure, and prevents the liquid from intruding into the inside, the containing body structured to be arranged in the container and immersed in the liquid;
   close contact means comprising a first magnetic part provided in the containing body, the close contact means being structured to bring a passing portion for the electromagnetic wave signal or the sound wave signal in the containing body into substantially close contact with an inner wall of the container; and
   a surface of the containing body is provided with a concave portion, and the sensor surface is exposed in the concave portion.

* * * * *